United States Patent
Celik et al.

(10) Patent No.: US 7,772,423 B2
(45) Date of Patent: Aug. 10, 2010

(54) PROCESS FOR THE PRODUCTION OF ALKYL ALKOXYACETATES

(75) Inventors: Fuat E. Celik, Berkeley, CA (US); Tae-Jin Kim, Lafayette, CA (US); Alexis T. Bell, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 40 days.

(21) Appl. No.: 12/257,163

(22) Filed: Oct. 23, 2008

(65) Prior Publication Data

US 2010/0105947 A1 Apr. 29, 2010

(51) Int. Cl.
 *C07C 67/36* (2006.01)
(52) U.S. Cl. ....................................................... 560/232
(58) Field of Classification Search ........................ None
See application file for complete search history.

(56) References Cited

U.S. PATENT DOCUMENTS 6,093,378 A 7/2000 Deebra et al.
2008/0045400 A1 2/2008 Rollins et al.

FOREIGN PATENT DOCUMENTS

EP 0088529 A2 9/1983

OTHER PUBLICATIONS

Celik et al., Journal of Molecular Catalysis A: Chemical, vol. 288, Issues 1-2, Jun. 3, 2008, pp. 87-96.*

* cited by examiner

*Primary Examiner*—Karl J Puttlitz
(74) *Attorney, Agent, or Firm*—Townsend and Townsend and Crew LLP.; M. Henry Heines

(57) ABSTRACT

A process for the production of lower alkyl alkoxyacetates, preferably methyl methoxyacetate, by reaction of a di-(lower alkoxy)methane, preferably dimethoxymethane, with the acid form of a medium-pore or large-pore zeolite catalyst, preferably the acid form of faujasite, ZSM-5, mordenite, or beta, in the gas phase at atmospheric or near-atmospheric pressures.

9 Claims, No Drawings

PROCESS FOR THE PRODUCTION OF ALKYL ALKOXYACETATES

BACKGROUND OF THE INVENTION

This invention relates to a new process for the production of lower alkyl alkoxyacetates, preferably methyl methoxyacetate, from di(lower alkoxy)methanes, preferably dimethoxymethane, that is carried out in the gas phase and at atmospheric or near-atmospheric conditions. Methyl methoxyacetate is an ether/ester of glycolic acid, and can be converted to glycolic acid and ultimately ethylene glycol by hydrogenation and hydrolysis, or reduced directly to ethylene glycol monomethyl ether, an important industrial solvent.

Acid-catalyzed formaldehyde carbonylation has been investigated as a means for producing carbon-carbon bonds for over sixty years. The product of this reaction, glycolic acid and its esters/ethers can be converted to ethylene glycol, an important industrial chemical used in polyester synthesis. Until now, such efforts have been carried out exclusively in the liquid-phase, typically requiring pressures of tens to hundreds of atmospheres of carbon monoxide to overcome its low solubility. The reaction proceeds by the Koch mechanism, in which protonated formaldehyde reacts with carbon monoxide to form an acyl carbocation, which is then hydrated to the carboxylic acid or ester product.

Production of methyl methoxyacetate by the reaction of dimethoxymethane with carbon monoxide has been described in several U.S. patents. In U.S. Pat. No. 2,273,269 (Johnson), the reaction is carried out at temperatures of from about room temperature to about 300° C. and pressures ranging from 5 and 1500 atmospheres, preferably 30-700 atmospheres. U.S. Pat. No. 3,948,977 (Suzuki) describes a process for carrying out this reaction using hydrogen fluoride as a catalyst, with carbon monoxide partial pressure of between 10 and 4000 psig. U.S. Pat. No. 4,501,917 (Schmidt et al.) used organic ion exchange materials as the catalyst, carrying out the process in an autoclave under pressure. In all of these processes, the reaction is conducted in liquid phase at elevated pressures.

Some other processes for production of methyl methoxyacetate include reaction of methanol with carbon monoxide in the presence of a hydrogen fluoride catalyst and an oxidizing agent (Threlkel, U.S. Pat. No. 4,482,735) and reaction of methoxy chloroacetate with an alkali metal methoxide (Kleemiss et al., U.S. Pat. No. 6,143,920). However, the first of these is a high pressure, batch liquid phase process and the second uses very expensive raw materials and involves complex processing.

BRIEF SUMMARY OF THE INVENTION

This invention comprises a process for the production of lower alkyl alkoxyacetates, preferably methyl methoxyacetate, by reaction of a di-(lower alkoxy)methane, preferably dimethoxymethane, with a zeolite catalyst selected from faujasite, ZSM-5, mordenite, and beta, in the gas phase at atmospheric or near-atmospheric pressures.

DETAILED DESCRIPTION OF THE INVENTION

As described in the examples that follow, dimethoxymethane (DMM) can be carbonylated to methyl methoxyacetate (MMAc) using a zeolite catalyst selected from faujasite (FAU), ZSM-5 (MFI), mordenite (MOR) and beta (BEA), at low temperature (preferably 90-150° C.) and preferably at atmospheric or near atmospheric pressure. The rate of the competing reaction/disproportionation of DMM to produce dimethyl ether (DME) and methyl formate (MF) byproducts can be kept low by selection of appropriate reaction conditions.

The process generally can be carried out in fixed-bed, fluidized-bed, or moving bed reactors, with appropriate separation of products and recycle of unreacted materials or byproducts where desired. In general, temperatures range from about 70 to about 200, preferably from about 90 to about 150° C., and pressures range from about 1 to about 100, preferably from about 2 to about 30 atm. Most preferably the process is carried out at near-atmospheric pressure, with "near-atmospheric" meaning from about 2 to about 5 atm. The feed gases for the process consist of carbon monoxide, DMM, and inert gases, preferably consisting of carbon monoxide and DMM only. The molar fractions of carbon monoxide range from about 50 to about 99.99%, preferably from about 90 to about 99.99%, most preferably from about 98 to about 99.99%.

Zeolites useful in this process include the acid forms of faujasite, ZSM-5, mordenite, and beta. The zeolites overall can be characterized as the proton form by Fourier transform infra-red spectroscopy. Other zeolites with pore openings of 4-5 Å and larger (ring systems possessing ten or more T-atoms), i.e. the acid forms of medium-pore and large-pore zeolites should also be effective in this process. Zeolites having substitution of aluminum in the framework with other suitable cations such as boron and gallium should also be effective in this process.

The following examples describe the process as applied to the production of methyl methoxyacetate from dimethoxymethane. However, the process is also useful for production of other lower alkyl lower alkoxyacetates from di(lower)alkoxymethanes, for instance ethyl ethoxyacetate from diethoxymethane. By "lower alkyl" and "lower alkoxy" are meant $C_1$-$C_4$ moieties. Preferably both alkoxy moieties of the dialkoxymethane are identical so that mixtures of products are less likely to be produced. The examples that follow are presented as illustrative of the invention, but in no way limit the nature of the invention.

EXAMPLE 1

$NH_4$-ZSM-5 zeolite (Si/Al 13.5, Alsi-Penta), was heated for 3 h at 773 K (2 K $min^{-1}$ ramp rate) in 100 $cm^3$ $min^{-1}$ dry air to convert it to the $H^+$ form and remove water.

0.05 g of the dried material was packed into a quartz microreactor with quartz wool to keep the catalyst in place. The catalyst was pretreated for 3 h at 773 K in dry air (100 $cm^3$ $min^{-1}$) to remove residual moisture, and cooled to 50° C. in UHP He (50 $cm^3$ $min^{-1}$, Praxair). 20 $cm^3$ $min^{-1}$ of CO (99.99% pure research grade, Praxair) was bubbled through a stainless steel saturator filled with dimethoxymethane (DMM) (99%, Sigma-Aldrich) and chilled to −20° C. to provide the desired vapor pressure. 78 $cm^3$ $min^{-1}$ of additional CO were mixed with the saturator exit flow before passing the combined gas flow (100 $cm^3$ $min^{-1}$) through the packed microreactor. The temperature of the catalyst bed was monitored by a quartz-sheathed K-type thermocouple. Reaction products were analyzed by using an Agilent 6890n GC equipped with an HP-PLOT Q bonded polystyrene-divinylbenzene capillary column connected to a flame ionization detector. The reaction temperature was increased by 10° C. every 45 minutes while products were being analyzed.

The maximum MMAc formation rate of 1.4 mmol (mmol Al h)$^{-1}$ was observed at 110° C., with a selectivity of 6.4% and conversion of 38%. At this temperature the DME formation rate was 21 mmol (mmol Al h)$^{-1}$ and the MF formation was 9.6 mmol (mmol Al h)$^{-1}$.

EXAMPLE 2

NH$_4$-ZSM-5 zeolite (Si/Al 12.5, Alsi-Penta) was treated by the procedure in Example 1. 0.08 g of this material was loaded into a quartz microreactor and subjected to the conditions of Example 1, except that 40 cm$^3$ min$^{-1}$ of CO was bubbled through the saturator and 156 cm$^3$ min$^{-1}$ of CO was added to bring the total gas flow rate to 200 cm$^3$ min$^{-1}$. A needle valve located downstream of the reactor was throttled to bring the total system pressure to 2 atm. The system pressure was monitored using a pressure transducer.

The maximum MMAc formation rate of 3.4 mmol (mmol Al h)$^{-1}$ was observed at 150° C., with a selectivity of 12% and conversion of 55%. At this temperature the DME formation rate was 25 mmol (mmol Al h)$^{-1}$ and the MF formation was 13 mmol (mmol Al h)$^{-1}$.

The maximum selectivity to MMAc of 40% was observed at 90° C., with a rate of 1.3 mmol (mmol Al h)$^{-1}$ and conversion of 7.8%. At this temperature the DME formation rate was 2.0 mmol (mmol Al h)$^{-1}$ and the MF formation rate was 1.0 mmol (mmol Al h)$^{-1}$.

EXAMPLE 3

NH$_4$-Mordenite zeolite (Si/Al 10, Alsi-Penta) was treated by the procedure in Example 1. 0.05 g of this material was loaded into a quartz microreactor and subjected to the conditions of Example 1.

The maximum MMAc formation rate of 3.8 mmol (mmol Al h)$^{-1}$ was observed at 90° C., with a selectivity of 23% and conversion of 38%. At this temperature the DME formation rate was 12 mmol (mmol Al h)$^{-1}$ and the MF formation was 7.4 mmol (mmol Al h)$^{-1}$.

EXAMPLE 4

NH$_4$-Mordenite zeolite (Si/Al 10, Alsi-Penta) was treated by the procedure in Example 1. 0.05 g of this material was loaded into a quartz microreactor and subjected to the conditions of Example 2 except that 60 cm$^3$ min$^{-1}$ of CO was bubbled through the saturator and an 238 cm$^3$ min$^{-1}$ of CO was added to bring the total gas flow rate to 300 cm$^3$ min$^{-1}$. A needle valve located downstream of the reactor was throttled to bring the total system pressure to 3 atm.

The maximum MMAc formation rate of 3.9 mmol (mmol Al h)$^{-1}$ was observed at 90° C., with a selectivity of 36% and conversion of 14%. At this temperature the DME formation rate was 6.7 mmol (mmol Al h)$^{-1}$ and the MF formation was 3.6 mmol (mmol Al h)$^{-1}$.

EXAMPLE 5

NH$_4$-Beta zeolite (Si/Al 12.5, Zeolyst) was treated by the procedure in Example 1. 0.07 g of this material was loaded into a quartz microreactor and subjected to the conditions of Example 2.

The maximum MMAc formation rate of 4.5 mmol (mmol Al h)$^{-1}$ was observed at 110° C., with a selectivity of 47% and conversion of 34%. At this temperature the DME formation rate was 11 mmol (mmol Al h)$^{-1}$ and the MF formation was 5.6 mmol (mmol Al h)$^{-1}$.

EXAMPLE 6

NH$_4$-Faujasite zeolite (Si/Al 30, Zeolyst) was treated by the procedure in Example 4. 0.05 g of this material was loaded into a quartz microreactor and subjected to the conditions of Example 4.

The maximum MMAc formation rate of 32 mmol (mmol Al h)$^{-1}$ was observed at 120° C., with a selectivity of 69% and conversion of 19%. At this temperature the DME formation rate was 15 mmol (mmol Al h)$^{-1}$ and the MF formation was 6.7 mmol (mmol Al h)$^{-1}$.

The maximum selectivity to MMAc of 79% was observed at 100° C., with a rate of 24 mmol (mmol Al h)$^{-1}$ and conversion of 13%. At this temperature the DME formation rate was 6.8 mmol (mmol Al h)$^{-1}$ and the MF formation rate was 2.9 mmol (mmol Al h)$^{-1}$.

The experimental work above shows that at steady state, methoxymethylene species can undergo carbonylation or disproportionation, and that the relative partial pressures of CO and DMM will control the selectivity between these competing reactions. Increasing $P_{CO}$ increases the rate of carbonylation. Reducing the concentration of methoxymethylene species also inhibits the rate of DMM disproportionation. Increasing $P_{DMM}$ increases the rate at which MMAc is released as a product, but also enhances the rate at which DMM disproportionation occurs.

The foregoing descriptions are offered primarily for purposes of illustration. Further modifications, variations and substitutions that still fall within the spirit and scope of the invention will be readily apparent to those skilled in the art. All such modifications coming within the scope of the appended claims are intended to be included therein.

All publications, patents, and patent applications cited herein are hereby incorporated by reference in their entirety for all purposes, except to the extent inconsistent with the disclosure herein.

What is claimed is:

1. A process for the production of a lower alkyl lower alkoxyacetate comprising reacting a di(lower alkoxy)methane with carbon monoxide while in contact with a zeolite catalyst selected from the acid forms of medium-pore and large-pore zeolites in the gas phase at a pressure of from about 1 atmosphere to about 100 atmospheres.

2. A process according to claim 1 wherein the zeolite is H-ZSM-5.

3. A process according to claim 1 conducted at atmospheric pressure.

4. A process according to claim 1 wherein the pressure is from about 2 to about 30 atm.

5. A process according to claim 1 wherein the pressure is from about 2 to about 5 atm.

6. A process according to claim 1 wherein the temperature is from about 70 to about 200° C.

7. A process according to claim 1 wherein the temperature is from about 90 to about 150° C.

8. A process according to claim 1 wherein the zeolite is selected from the acid forms of faujasite, ZSM-5, mordenite and beta.

9. A process according to claim 1 wherein the di(lower alkoxy) methane is dimethoxymethane and the lower alkyl lower alkoxyacetate is methyl methoxyacetate.

* * * * *